(12) United States Patent
Das et al.

(10) Patent No.: US 10,730,891 B2
(45) Date of Patent: Aug. 4, 2020

(54) COMPOUND FOR SELECTIVE DETERMINATION OF FREE CYSTEINE AND A PROCESS FOR THE PREPARATION THEREOF

(71) Applicant: COUNCIL OF SCIENTIFIC & INDUSTRIAL RESEARCH, New Delhi (IN)

(72) Inventors: Amitava Das, Maharashtra (IN); Firoj Ali, Maharashtra (IN); Upendar Reddy Gandra, Maharashtra (IN); Anila Hoskere Ashok, Maharashtra (IN); Samit Chattopadhyay, Maharashtra (IN); Nandaraj Taye, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 275 days.

(21) Appl. No.: 15/749,160

(22) PCT Filed: Jul. 29, 2016

(86) PCT No.: PCT/IN2016/050254
§ 371 (c)(1),
(2) Date: Jan. 31, 2018

(87) PCT Pub. No.: WO2017/021980
PCT Pub. Date: Feb. 9, 2017

(65) Prior Publication Data
US 2018/0354975 A1    Dec. 13, 2018

(30) Foreign Application Priority Data

Jul. 31, 2015 (IN) .......................... 2354/DEL/2015

(51) Int. Cl.
*C07F 5/02* (2006.01)
*G01N 33/68* (2006.01)

(52) U.S. Cl.
CPC .......... *C07F 5/022* (2013.01); *G01N 33/6815* (2013.01)

(58) Field of Classification Search
CPC ........................... C07F 5/022; G01N 33/6815
See application file for complete search history.

(56) References Cited

U.S. PATENT DOCUMENTS

2004/0076547 A1*  4/2004  Carney .............. A61B 10/0045
                                                422/82.08
2012/0070382 A1*  3/2012  Liu ........................ B82Y 10/00
                                                   424/9.6

OTHER PUBLICATIONS

Reedy et al., "A Novel Fluorescence Probe for Estimation of Cysteine/Histidine in Human Blood Plasma and Recoginition of Endogenous Cysteine in Live Hct116 Cells", Chem. Commun., 2014, vol. 50, pp. 9899-9902.

Das et al., "Desigining a Thiol Specific Fluorescent Probe for Possible Use as a Reagent for Intercellular Detection and Estimation in Blood Serum: Kinetic Analysis to Probe the Role of Intramolecular Hydrogen Bonding", Org. Biomol. Chem., 2013, vol. 11, pp. 6604-6614.

Yang et al., "Conjugate Addition/Cyclization Sequence Enables Selective and Simultaneous Fluorescence Detection of Cysteine and Homocysteine", Angew. Chem. Int. Ed., 2011, vol. 50, pp. 10690-10693.

(Continued)

*Primary Examiner* — Lore R Jarrett
(74) *Attorney, Agent, or Firm* — Baker & Hostetler LLP

(57) ABSTRACT

The present invention relates to a compound (L) for selective determination of free cysteine and a process for the preparation thereof.

(Continued)

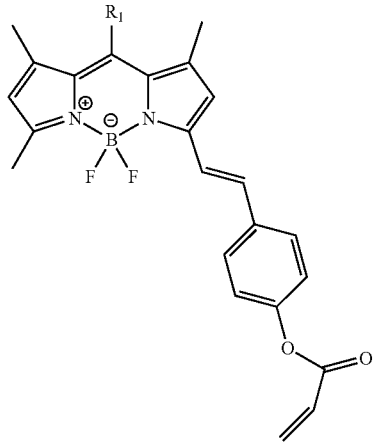

FORMULA (L)

wherein R1 is selected from benzene, toluene, naphthalene and pyrene.

4 Claims, 9 Drawing Sheets

(56) References Cited

OTHER PUBLICATIONS

Das et al., "New Chemodosimetric Reagents as Ratiometric Probes for Cysteine and Homocysteine and Possible Detection in Living Cells and in Blood Plasma", Chem. Eur. J., 2012, vol. 18, pp. 15382-15393.

* cited by examiner

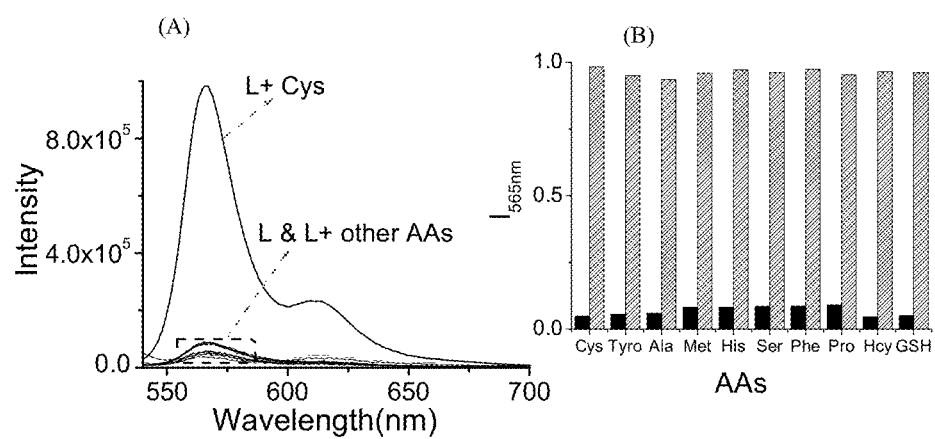
Figure: 1

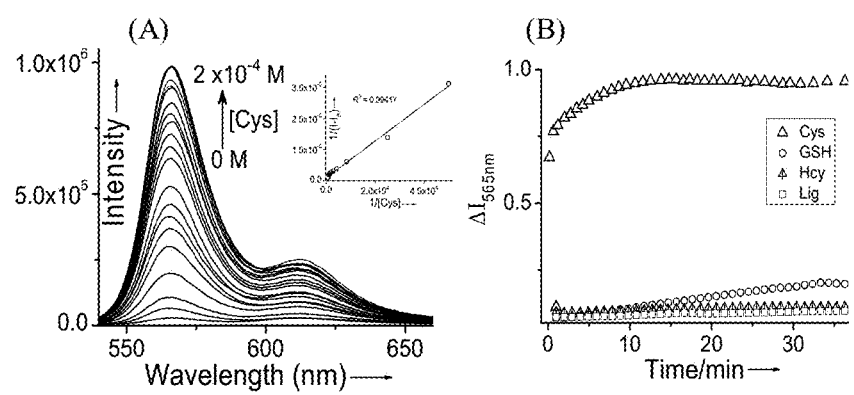
Figure: 2

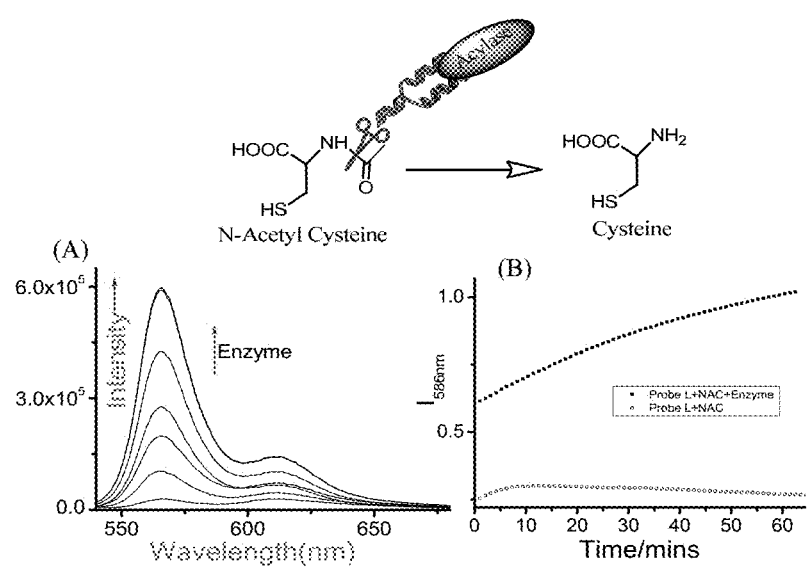
Figure: 3

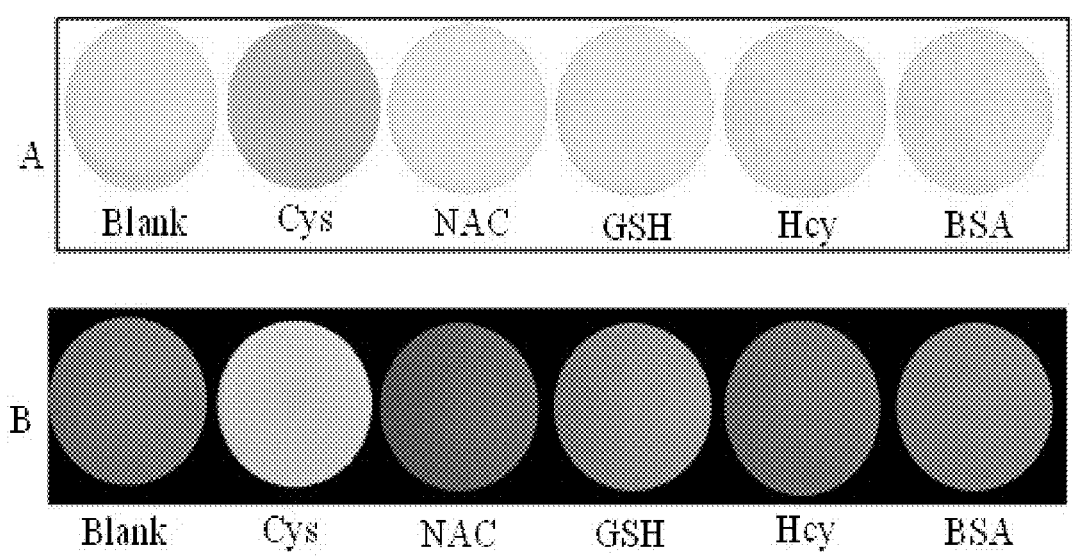
Figure: 4

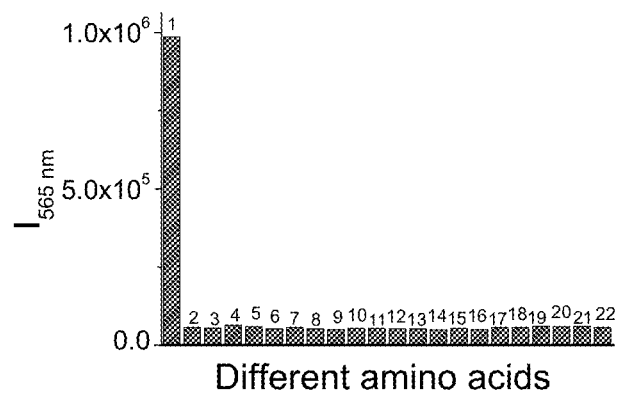
Figure: 5

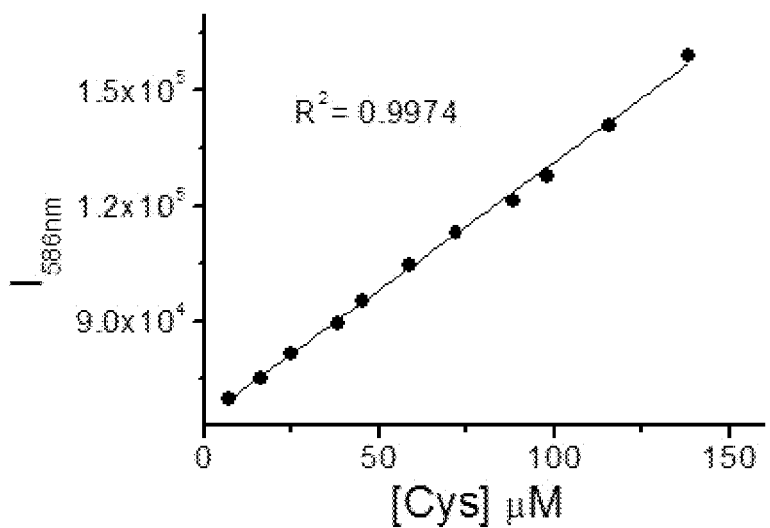
Figure: 6

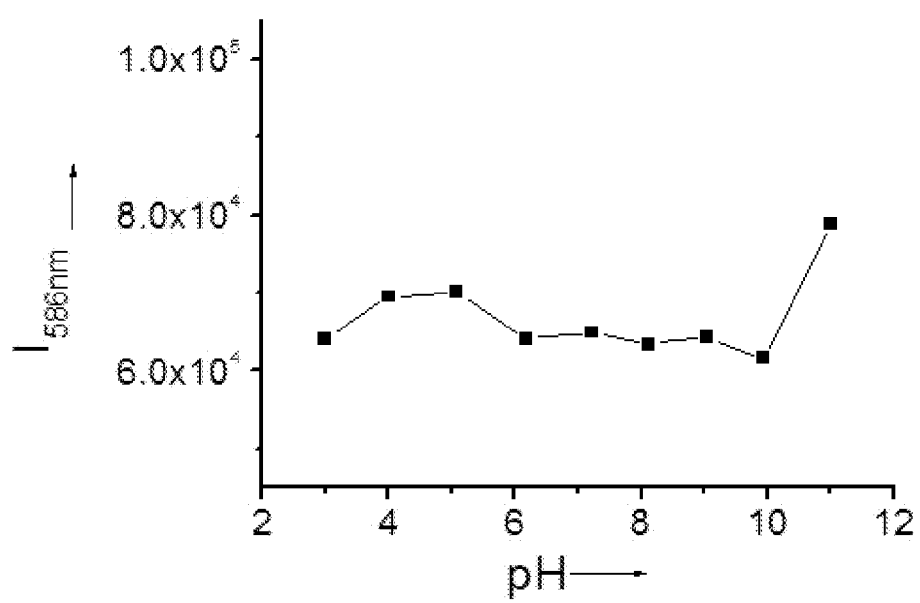
Figure: 7

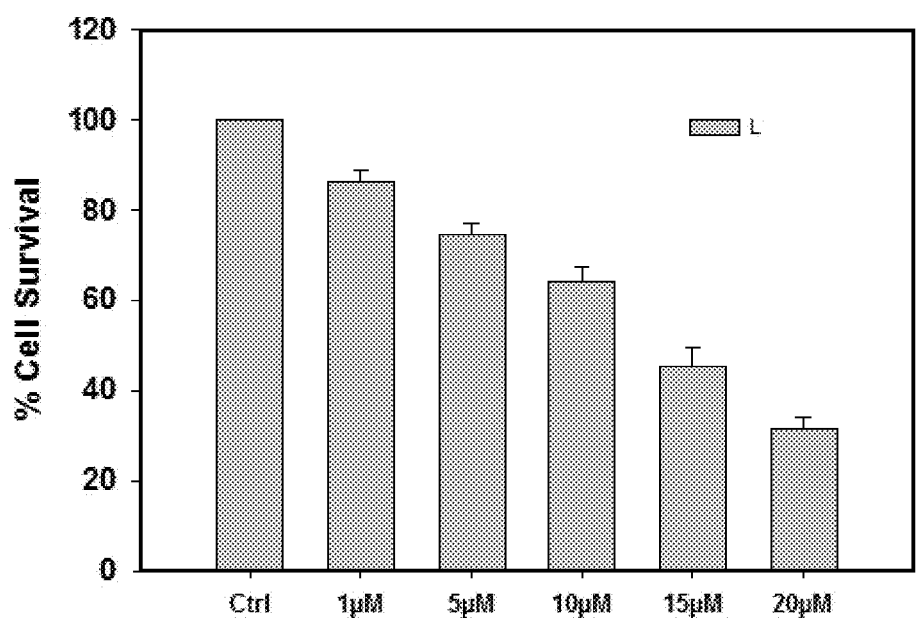
Figure: 8

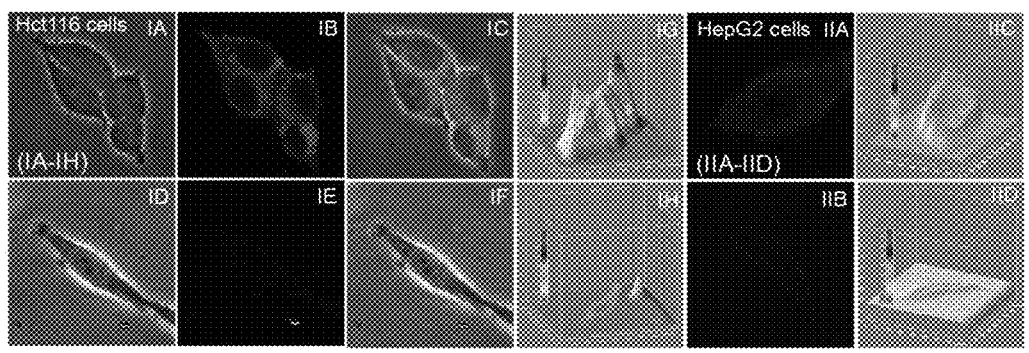
Figure: 9

COMPOUND FOR SELECTIVE DETERMINATION OF FREE CYSTEINE AND A PROCESS FOR THE PREPARATION THEREOF

FIELD OF THE INVENTION

The present invention relates to a compound of general formula (L) for selective determination of free cysteine and a process for the preparation thereof.

FORMULA (L)

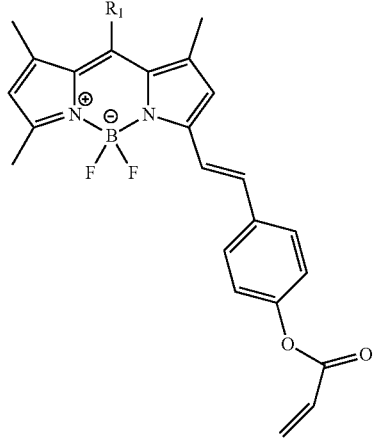

wherein R1 is selected from phenyl, toluene, naphthalene and pyrene.

BACKGROUND AND PRIOR ART OF THE INVENTION

Biological thiols such as Cysteine (Cys), Homocysteine (Hcy) and Glutathione (GSH) play crucial roles in maintaining cellular antioxidant defence system. Among them cysteine plays many important roles in living systems. Cysteine is one of the three main precursors required for GSH synthesis. The deficiency of this compound causes many diseases such as slowed growth in children, depigmentation of hair, edema, liver damage, skin lesions, and weakness. An elevated level of Hcy is a risk factor for cardio-vascular disease, dementia and Alzheimer's disease. Abnormal levels of GSH is connected to many diseases such as HIV, cell death and aging. Thus, detection and discrimination of these thiol containing molecules are of great importance. Because of the similar structure and reactivity, distinction among biothiols is a challenging task. The respective concentration level of Cys and His in human plasma is typically 240-360 µM and 15-75 µM. Estimation of these amino thiols in human blood plasma is essential for understanding the role of these in the pathogenesis of vascular diseases.

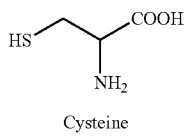

Cysteine

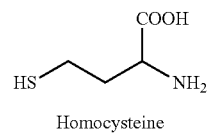

Homocysteine

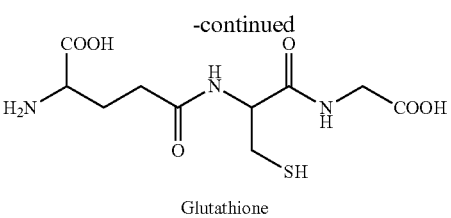

Glutathione

The past two decade has seen significant effort being devoted to the development of optical probes for the selective recognition of thiol containing amino acids. There are many strategies for sensing biothiols, based on Micheal addition, cyclization with aldehydes, disulfide cleavage and others.

Das et al. (*Chem. commun.*, 2014, 50, 9899-9902) discloses chemo dosimetric reagents for biothiol. A Cu (II)-complex based probe for detection of Cys and Histidine was reported.

P Das et al. (*Org. Biomol. Chem.*, 2013, 11, 6604-6614) reports a new and simple chemodosimetric probe $L_1 1$ is utilized for the selective detection of biothiols in the presence of other relevant amino acids under physiological conditions (pH=7.4). Furthermore, the studies with human blood plasma demonstrated the possibility of using this reagent for the quantitative optical detection of total biothiols in biological fluid.

X Yang et al. (*Angewandte Chemie International Edition*, Nov. 4, 2011, Volume 50, Issue 45, pages 10690-10693) reports a benzothiazole derivative used to detect cysteine (Cys) and homocysteine (Hcy) simultaneously in neutral media. The method involves thioether formation followed by cyclization to release 2-(2'-hydroxy-3'-methoxyphenyl) benzothiazole (HMBT) and a lactam.

P Das et al. (*Chemistry—A European Journal*, Nov. 26, 2012, Volume 18, Issue 48, pages 15382-15393) reports rationally designed and synthesized two new reagents L1 {(4-(1H-imidazo[4,5-f][1,10]phenanthrolin-2-yl)benzaldehyde)} and L2 {(4-(6,11-dioxo-6,11-dihydro-3H-anthra[1,2-d]imidazol-2-yl)benzaldehyde)}, each bearing a pendant aldehyde functionality. This aldehyde group can take part in cyclization reactions with 13- or γ-amino thiols to yield the corresponding thiazolidine and thiazinane derivatives, respectively. These two chemodosimetric reagents could be used for the quantitative detection of cysteine present in blood plasma by using a pre-column HPLC technique.

However, the development of probes for specific discrimination of biothiols is an unmet need in the art. Probes that are selective to any one of these amino biothiols are very rare in literature. Probes that give specific response with colour change as well as emission change are much needed. Especially those probes which allows real time monitoring without the aid of any instrumental techniques are highly recommended as for as the practical utility is concerned. There are no reports on detection of thiols using simple test strips. Particularly, a further challenge that is unaddressed in the art is that of a simple process for the determination of free cysteine.

Therefore, there is need in the art to develop a reagent for selective detection of free cysteine, especially with a high degree of selectivity towards free cysteine. Accordingly, the inventors of present invention developed a novel ligand for the selective detection of free cysteine.

OBJECTIVE OF THE INVENTION

The main objective of present invention is to provide a novel ligand of formula (L) useful for the selective detection of free cysteine and process for the preparation thereof.

Another objective of present invention is to provide a kit for the selective detection of free cysteine characterized in that the selectivity of novel ligand of formula (L) to cysteine is very high and a process for detection using the kit.

Yet another objective of present invention is to provide a visual as well as fluorescence test for detection of cysteine using novel ligand of formula (L).

SUMMARY OF THE INVENTION

Accordingly, the present invention provides a compound of general formula (L) which is useful for the selective detection of free cysteine and process for the preparation thereof.

FORMULA (L)

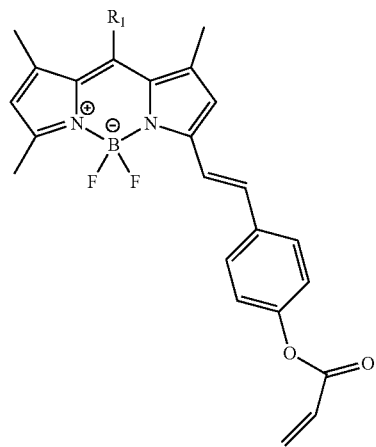

Wherein $R_1$ is selected from

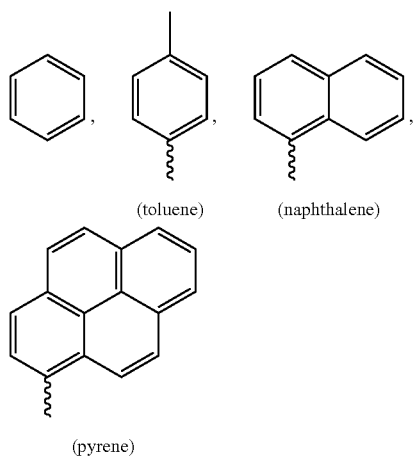

(toluene)  (naphthalene)

(pyrene)

The representative compounds of formula (L) being the ligand of formula (L) are;

A

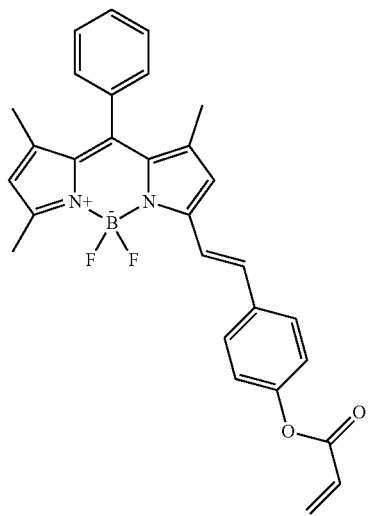

B

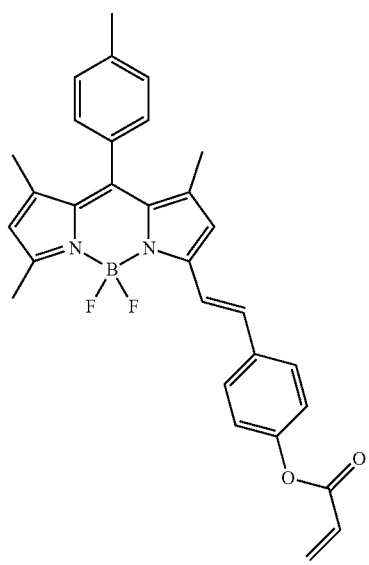

C

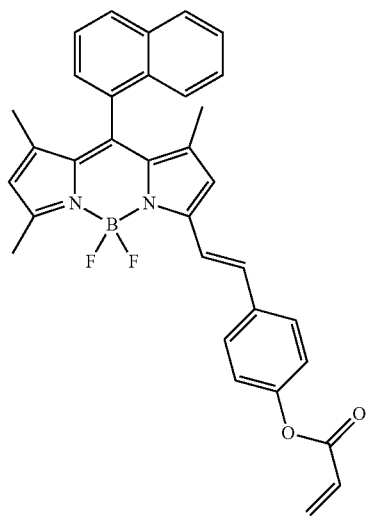

-continued

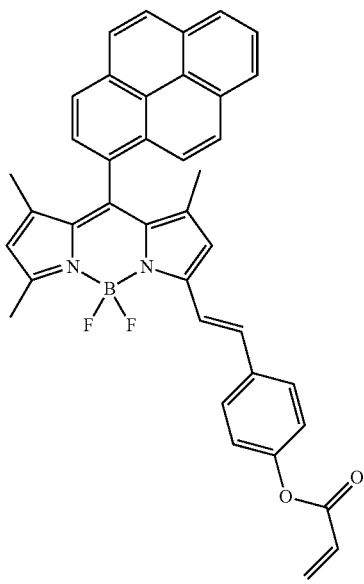

In an aspect, the present invention provides a kit for the selective detection of free cysteine characterized in that the selectivity of novel ligand of formula (L) to cysteine is 100% and a process for detection using the kit.

In another aspect, the present invention provides a visual as well as fluorescence test for detection of cysteine using novel ligands of formula (L).

Abbreviations Used:
GSH: Glutathione
Hcy: Homocysteine
Cys: Cysteine
NAC: N-Acetylcysteine
AAs: Aminoacids
Probe L: Novel ligand of formula (L)
HEPES: (4-(2-hydroxyethyl)-1-piperazineethanesulfonic acid)
BODIPY—Boron-dipyrromethene
DCM—Dicholomethane

BRIEF DESCRIPTION OF THE DRAWINGS

FIG. 1: (A) Change in emission spectrum ($\lambda_{ex}$ 530 nm) of L (10 uM) in presence and absence of different AAs (2 mM); (B) Emission response of L (10 uM) for Cys (200 uM) in presence of other amino acids (200 uM) in aq. HEPES buffer-acetonitrile medium at pH 7.2. Red bar indicates addition of Cys to the mixture and black bar represents emission response at 583 nm in absence of Cys.

FIG. 2: (A) Emission ($\lambda_{Ext}$: 530 nm) spectral pattern for L (10 uM) in presence of varying [Cys] (0-2 mM); Inset: B-H plot obtain from systematic emission titration of L with Cys; (B) Time dependent studies of L (10 uM) in presence and absence of 5 eqv of Cys, Hcy and GSH in aq. HEPES-acetonitrile (ACN) (9:1, v/v) medium at pH 7.2. $\lambda_{Ext}/\lambda_{em}$: 530/585 nm.

FIG. 3: (A) Emission response of probe L (10 uM) and NAC (2 mM) with various concentration acylase enzyme, Each spectra was recorded after 20 min at 37° C. at pH 7.2, $\lambda_{Ext}$ 530 nm; (B Emission intensity at 586 nm of probe L with NAC in absence and presence of enzyme vs. time plot.

FIG. 4: Visual (A) and Fluorescence (B) colour changes of probe L coated TLC plates in presence and absence of different analytes (Cys, NAC, GSH, Hcy and BSA). Fluorescence colour was recorded using UV lamp excitation at 365 nm.

FIG. 5: Emission response of L (10 µM) in the absence and presence of various amino acids (200 mole equiv. each). (From 1-23, Cysteine, L only, Homocysteine, Glutathione, Histidine, Leucine, Methionine, Phenylalanine, Tryptophon, Tyrosine, Valine, Alanine, Arginine, Glycine, Glutamine, Proline, Serine, Aspartic acid, Glutamic acid, Threonine, Isoleucine, Lysine). In 10 mM HEPES: $CH_3CN$ (9:1, v/v) at pH 7, $\lambda_{Ext}$=530 nm.

FIG. 6: Fluorescence intensity at 586 nm upon addition of Cys (0-150 µM) in 10 mM HEPES: ACN (9:1, v/v) at pH7, $\lambda_{Ext}$=530 nm.

FIG. 7: Change of emission intensity of probe L with pH.

FIG. 8: MTT assay to determine the cell viability percentage in Hct116 colon cancer cells.

FIG. 9: (I) CLSM images of Hct116 cells (IA-IH), cells incubated with 1 µM of L, (IA): bright field images, (IB): dark field image and (IC): overlay images of (IA) & (IB); Cells pre-treated with 1 mM of NEM then incubated with 1 µM of L, (ID): bright field image, (IE): dark field image, (IF): overlay of (ID) & (IE). (IG) and (IH) were 3D intensity plot of (IB) & (IE) respectively; (II) CLSM images of live HepG2 cells: (IIA) & (IIB) dark field images of cells treated with 1 mM NEM, washed and then treated with (IIA) or without (IIB) 25 µM NAC for 1 h, followed by incubation of 1 µM of L for 20 min and (IIC) & (IID) are respective 3D intensity profile plot of images (II)A & (II)B. (II)A & (II)C revealed the generation of Cys from NAC by aminoacylase-I present in HepG2 cells, $\lambda_{Ext}/\lambda_{Em}$: 530/573 nm.

FIG. 9: (A) Hct116 cells stained with 1 µM of L in presence of ER tracker green; (i) Intensity profile of ROIs across cells: red line represent intensity of L and green line indicate intensity for ER Tracker green; (B) co-localization experiment: Cells were co-stained with L, ER tracker green and DAPI; $\lambda_{Ext}/\lambda_{Em}$: 530/573 nm.

DETAILED DESCRIPTION OF THE INVENTION

For the purpose of this invention, the expression "probe L" and "novel ligand of formula (L)" are used interchangeably throughout the specification and both having the same meaning.

The present invention provides a novel ligand of formula (L) which is useful for the selective detection of free cysteine and process for the preparation thereof. This probe L is used for the detection of free cysteine by a simple, convenient, selective and fast visual method in aqueous medium as well as biological fluids. The present invention also provides a kit for the selective detection of free cysteine characterized in that the selectivity of novel ligand of formula (L) to cysteine is 100% and a process for detection using the kit.

Accordingly, the main embodiment of the present invention provides a compound for selective determination of free cysteine having general formula (L)

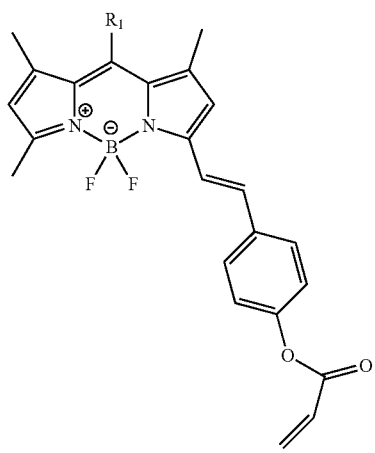
wherein R₁ is selected from
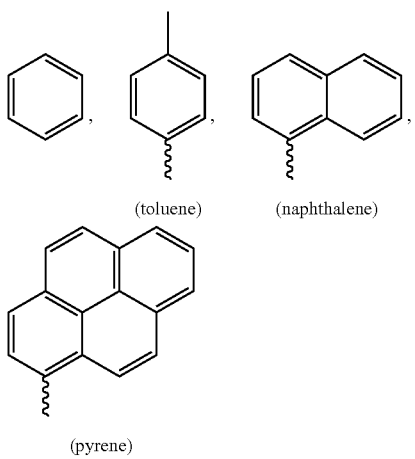
Another embodiment of the present invention provides a novel ligand of formula (L) useful for the detection of free cysteine.
Formula (L)
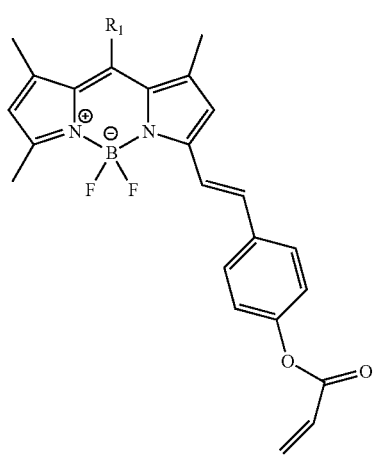
wherein R₁ is selected from
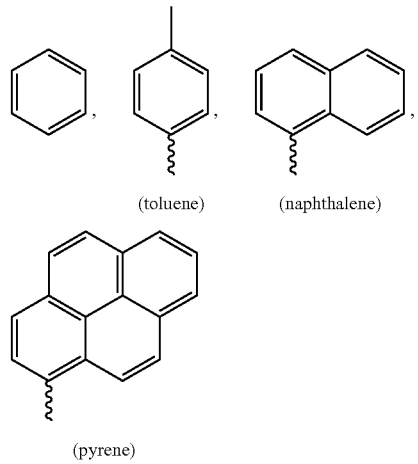
In another embodiment of the present invention the compounds of formula (L) comprises:
A
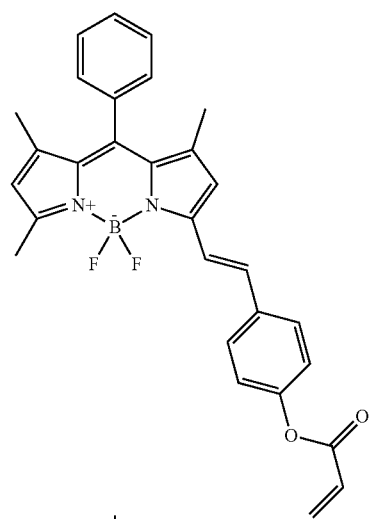
B
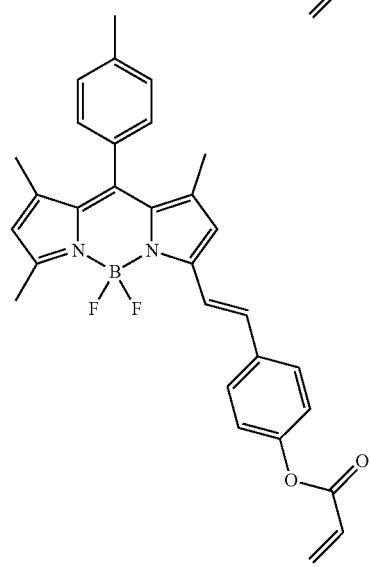

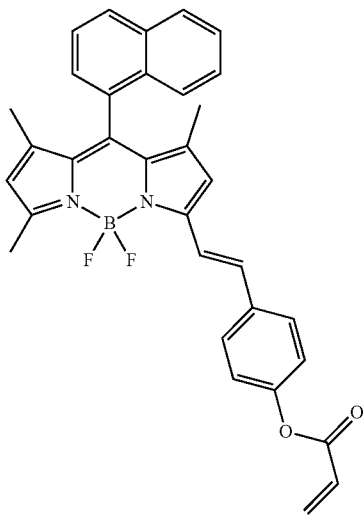

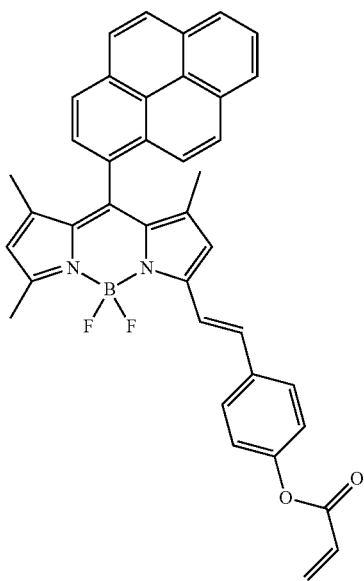

Another embodiment of the present invention provides a process for the preparation of compound of formula (L), comprising the steps of:

(i) Refluxing boron-dipyrromethene (BODIPY) of formula R″ with 4-hydroxybenzaldehyde, piperidine and glacial acetic acid in toluene to obtain compound of formula R′;

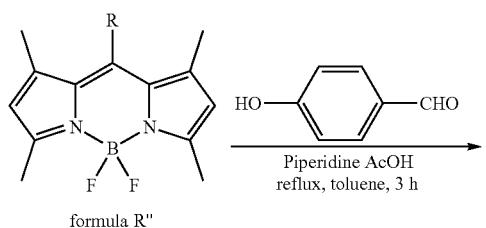

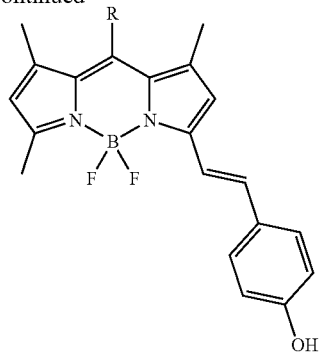

wherein R represent phenyl, toluene, naphthalene and pyrene;

(ii) Reacting the compound of formula R′ with acryloyl chloride in dichlotomethane (DCM) at room temperature to obtain ligand of formula (L)

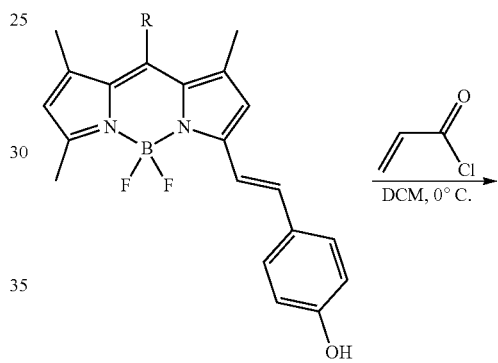

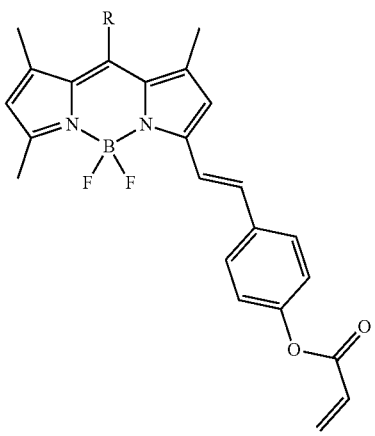

formula L wherein R represent phenyl, toluene, naphthalene and pyrene.

Another embodiment of the present invention provides a process for the synthesis of ligand of formula (L) comprising the steps of:

a) Refluxing the reaction mixture comprising BODIPY of formula R″, 4-hydroxybenzaldehyde, piperidine and glacial acetic acid in toluene for 3 h at 110° C. to obtain compound of formula (R′).

b) Reacting the compound of formula R' with acryloyl chloride in dicholomethane (DCM) at room temperature to obtain ligand of formula (L).

In another embodiment of the present invention, a mixture of BODIPY (boron-dipyrromethene) (400 mg, 1.23 mmol), 4-hydroxybenzaldehyde (165 mg, 1.35 mmol), 0.9 ml piperidine and 0.6 ml glacial acetic acid was reflux in 30 ml toluene in a Dean-Stark apparatus for 3 h. Then water was added into it and crude organic layer was extracted with dichloromethane. The organic layer was collected and dried over anhydrous sodium sulphate and solvent was removed under reduced pressure. It was then subjected to column chromatography using silica gel (100-200 mesh) as stationary phase and 10% EtOAc in hexane as mobile phase to get compound R' as red solid.

In yet another embodiment, BODIPY compound R' (30 mg, 0.07 mmol) was dissolved in 10 ml anhydrous dichloromethane in a 100 ml round bottom two neck flask. Then 100 uL of $Et_3N$ was added to the reaction mixture and allowed to stir for 10 mins at room temperature under $N_2$ atmosphere. 20 uL of acryloyl chloride was added to this and resulting mixture was stirred at room temperature until all the starting material was consumed monitored by TLC. Then water was added to it and organic layer was extracted using dichloromethane. The organic layer was collected and dried over anhydrous sodium sulphate and solvent was removed under reduced pressure. It was then subjected to column chromatography using silica gel (100-200 mesh) as stationary phase and 5% EtOAc in hexane as mobile phase to get probe L as solid as 70% yield.

In yet another embodiment, the present invention discloses the process for the synthesis for novel ligand of formula (L) is depicted in scheme 1 below;

Scheme 1

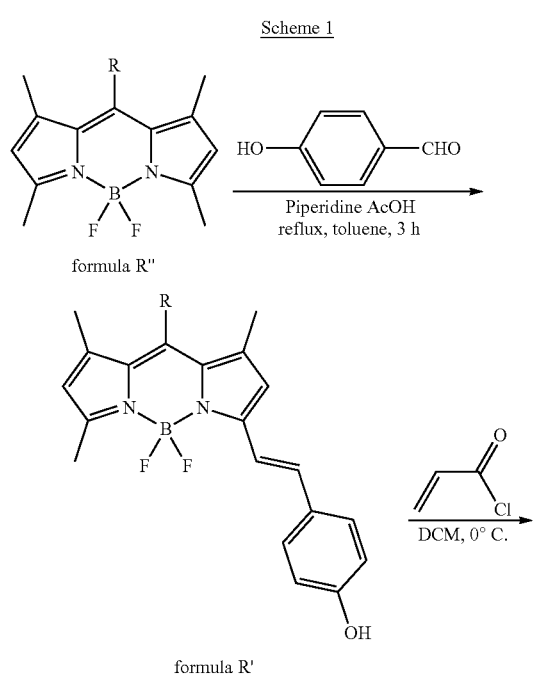

formula R'

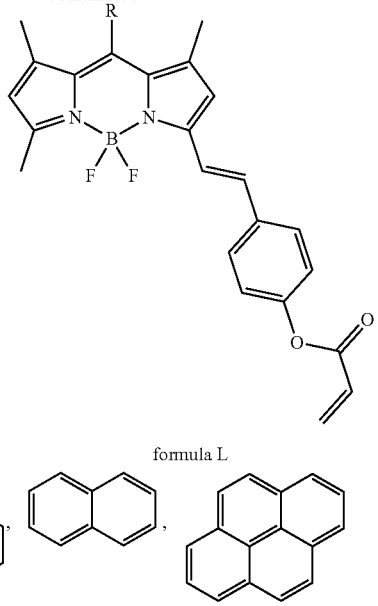

formula L

R =

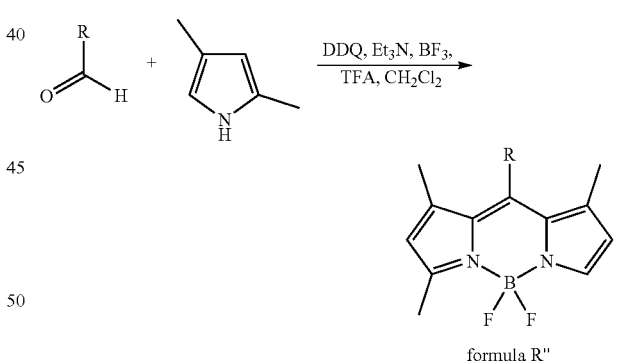

The BODIPY of formula R" is prepared by known methods comprising reacting aldehyde or acid chloride with 2, 4 dimethyl pyrrole. The aldehyde is used appropriately to obtain the BODIPY of formula R" wherein the substituent R represents toluene, naphthalene and pyrene. The acid chloride is selected from benzoyl chloride to obtain BODIPY of formula R" wherein the substituent R is phenyl.

Accordingly, the process for preparation of BODIPY of formula R", wherein R represents toluene, naphthalene and pyrene comprises reacting the corresponding aldehyde with 2, 4 dimethyl pyrrole in presence of DDQ, $Et_3N:BF_3$ in presence of trifluroacetic acid and DCM.

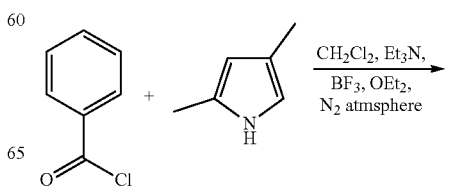

The process for preparation of BODIPY of formula R", wherein R is phenyl comprises reacting benzoyl chloride and 2, 4 dimethyl pyrrole in presence of triethylamine, $BF_3.OEt_2$ in dichloromethane under nitrogen atmosphere.

-continued

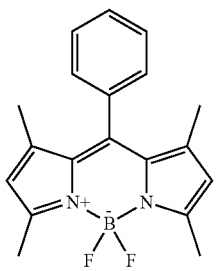

Another embodiment of the present invention provides for a diagnostic kit for selective detection of free cysteine.

In another embodiment of the present invention, the diagnostic kit comprises:
(a) Ligand of Formula (L)
(b) HEPES aqueous buffer medium
(c) TLC Test strips
(d) HEPES:acetonitrile medium
(e) Instruction manual Another embodiment of the present invention provides a method for selective detection of free cysteine using the diagnostic kit comprising;
(i) Dissolving 500 μl of $1 \times 10^{-4}$ M of ligand of formula (L) in 4.5 ml of 10 mM HEPES aqueous buffer medium of pH 7.2 to obtain $1 \times 10^{-5}$ M ligand concentration;
(ii) preparing the stock solution of $1 \times 10^{-2}$ M analytes in aqueous HEPES buffer medium at pH 7.2;
(iii) TLC test strips; and
(iv) performing the photo physical studies for detection of free cysteine in HEPES:acetonitrile medium (9:1, v/v) at pH 7.2 as per the instruction manual.

In another embodiment of the present invention the emission response of ligand L with various amino acids (AAs) as well as anionic analytes in aqueous buffer-acetonitrile (9:1, v/v) at pH 7.2 solution (FIG. 1) is studied. FIG. 1 shows that emission spectrum recorded for L (10 uM) and L+AAs (200 uM) except Cys does not shows any prominent changes, only after addition cysteine (Cys), probe L shows a fluorescence turn on response at 583 nm upon $\lambda_{ex}$ at 530 nm under specified experimental condition. Further emission response of probe L towards Cys in presence of other AAs is also carried out under identical condition (FIG. 1). These findings suggested L is a selective fluorescence turn on probe for Cys in aqueous HEPES buffer medium. Probe L does not show emission changes in presence of Hcy, GSH, N-acetyl cysteine (NAC) as well as cysteine bound protein like BSA, upon $\lambda_{ex}$ at 530 nm (FIG. 1). Thus L can specifically detect Cys, over other biothiols, NAC and cysteine bound protein.

In another embodiment of the present invention time dependent fluorescence assay of probe L (10 uM) is carried out in presence of 5 eqv. of Cys, Hcy and GSH by monitoring emission changes at $\lambda_{em}$ at 583 nm in aq. HEPES buffer-acetonitrile (9:1, v/v) at pH 7.2 medium (FIG. 2). FIG. 2 reveals that emission intensity reaches maximum within 1 min after addition of 2 mM of Cys, whereas no prominent changes is observed for Hcy and GSH even after 40 min of incubation under identical condition.

In another embodiment of the present invention the fluorescence intensity of probe L is determined to be linearly proportional with Cys concentration and the detection limit of free cysteine by the fluorescence spectroscopy method is found to be 15 nM. The effect of pH towards probe L indicated ligand L is stable up to pH 9. FIG. 3 indicates that with increase in acylase concentration, probe L gives fluorescence turn on response with fixed initial concentration of NAC and L. The probe L may be used for monitoring enzymatic generation of Cys.

In another embodiment, probe L is used for the detection of free cysteine by a simple, convenient, selective and fast visual method in aqueous medium as well as biological fluids. Accordingly, a TLC plate is immersed into acetonitrile solution of probe L (5 μL) and dried. This TLC plate coated with probe L is exposed to aqueous solution of different analytes under identical condition. Upon addition of Cysteine solution a prominent change in fluorescence (green to reddish) using UV lamp with excitation at 365 nm and little colour (light pink to dark pink) are observed in TLC plate. In case of other analytes including Hcy, GSH, NAC, and BSA protein (contain terminal Cys residue) no detectable changes are induced.

In another embodiment, the probe L is tested for biological properties. In a preferred embodiment, the probe L is tested for cytotoxicity and at micro molar concentration of probe L used for cellular studies 85% of cell servility. The in vitro cytotoxicity of L on Hct116 cells (Colon cancer cell) are determined by conventional MTT (3-(4, 5-Dimethylthiazol-2-yl)-2, 5-diphenyltetrazolium bromide, a yellow tetrazole) assay. Hct116 colon cancer cells ($7 \times 10^3$) are seeded in each well of a 96 well plate and cultured in a 37° C. incubator supplied with 5% $CO_2$. Cells are maintained in DMEM medium, supplemented with 10% Foetal Bovine Serum and 100 Units of Penicillin Streptomycin antibiotics. After 24 hours the cells are treated with different concentrations of the L in triplicates for 12 hours. After treatment cells are added with 0.5 μg/ml of MTT reagent. The plate is then incubated for 4 hours at 37° C. 100 μl of Isopropyl Alcohol is added to each well.

The following examples are given by way of illustration and therefore should not be construed to limit the scope of the present invention:

EXAMPLES

Example 1: Synthesis of R'

A mixture of BODIPY (boron-dipyrromethene) (400 mg, 1.23 mmol), 4-hydroxybenzaldehyde (165 mg, 1.35 mmol), 0.9 ml piperidine and 0.6 ml glacial acetic acid was reflux in 30 ml toluene in a Dean-Stark apparatus for 3 h. Then water was added into it and crude organic layer was extracted with dichloromethane. The organic layer was collected and dried over anhydrous sodium sulphate and solvent was removed under reduced pressure. It was then subjected to column chromatography using silica gel (100-200 mesh) as stationary phase and 10% EtOAc in hexane as mobile phase to get compound R' as red solid. Yield: 56%; $^1$H NMR (500 MHz, CDCl$_3$, J in Hz, δ ppm): 7.52 (1H, d, J=16.5), 7.47 (5H, m), 7.3 (2H, d, J=8), 7.18 (1H, d, J=16), 6.83 (2H, d, J=8.5), 6.58 (1H, s), 5.99 (1H, s), 5.4 (1H, s), 2.59 (3H, s), 1.42 (3H, s), 1.38 (3H, s); $^{13}$C NMR (125 MHz, CDCl$_3$, δ ppm): 156.80, 154.68, 153.47, 142.74, 142.40, 140.08, 136.24, 135.13, 132.84, 131.68, 129.38, 129.22, 129.09, 128.93, 128.25, 121.14, 117.55, 116.90, 115.82, 14.69, 14.59, 14.32. HRMS (ESI): m/z calculated for $C_{26}H_{23}BF_2N_2O$ [M+H]: 429.1872, found 429.1943.

Example 2: Synthesis of Probe L

In a 100 ml round bottom two neck flask BODIPY compound R' (30 mg, 0.07 mmol) was dissolved in 10 ml anhydrous dichloromethane. Then 100 uL of Et$_3$N was added to the reaction mixture and allowed to stir for 10 mins at room temperature under $N_2$ atmosphere. 20 uL of acryloyl chloride was added to this and resulting mixture was stirred at room temperature until all the starting material was consumed monitored by TLC. Then water was added to it and organic layer was extracted using dichloromethane. The organic layer was collected and dried over anhydrous sodium sulphate and solvent was removed under reduced pressure. It was then subjected to column chromatography using silica gel (100-200 mesh) as stationary phase and 5% EtOAc in hexane as mobile phase to get probe L as solid as 70% yield. $^1$H NMR (500 MHz, CDCl$_3$, J in Hz, δ ppm): 7.57 (1H, s), 7.53 (3H, d, J=8.2), 7.41 (3H, d, J=5.8), 7.25-7.21 (2H, m), 7.13 (1H, d, J=16.3), 7.07 (2H, d, J=8.4), 6.56 (1H, s), 6.52 (1H, s), 6.25 (1H, dd, J=17.3, 10.5), 5.95 (2H, d, J=11.1), 2.52 (3H, s), 1.35 (3H, s), 1.31 (3H, s); $^{13}$C NMR (125 MHz, CDCl$_3$, δ ppm): 164.35, 155.92, 152.21, 150.90, 143.27, 142.34, 140.65, 135.03, 134.69, 134.39, 132.78, 132.05, 129.15, 129.01, 128.44, 128.14, 127.86, 121.88, 121.55, 119.41, 117.48, 14.79, 14.57, 14.42. HRMS (ESI): m/z calculated for $C_{29}H_{26}BF_2N_2O_2$ [M+H]: 483.1977 found 483.2057.

Example 3: General Experimental Procedure for UV-Vis and Fluorescence Studies Stock solution of probe L ($1\times10^{-4}$ M) was prepared in HPLC grade acetonitrile. All the analytes stock solution ($1\times10^{-2}$ M) was prepared in aqueous HEPES buffer medium at pH 7.2. 500 μL of this stock solution of probe L was added to 4.5 ml of HEPES (10 mM) aqueous buffer medium having solution pH 7.2 to make the effective ligand concentration of $1\times10^{-5}$ M. This solution was used for all the photophysical studies. All the photo physical studies were performed in HEPES:acetonitrile medium (9:1, v/v) at pH 7.2. The detection limit was calculated based on the fluorescence titration. To determine the S/N ratio, the emission intensity of L without Cys was measured 10 times and the standard deviation of blank measurements was determined. The detection limit (DL) of L for Cys was determined from the following equation:

$$DL = K*Sb1/S,$$

Where K=2 or 3 (we took 3 in this case);
Sb1 is the standard deviation of the blank solution;
S is the slope of the calibration curve.
From the graph we get slope=$4.99\times10^8$, and Sb1 value is 2.49
Thus using the formula we get the Detection Limit=$15\times10^{-9}$M.

Example 4: Preparation of TLC Test Strips

TLC test strips were prepared by coating 5 μM of probe solution in acetonitrile on silica TLC plates. 5 μl of Cys ($1\times10^{-1}$M) in 10 mM aq. HEPES buffer (pH 7) was added on it, dried and the visual as well as fluorescence colour changes were observed after 5 min. The same was repeated for Hcy, GSH and other analytes as well.

Example 5: General Procedure for Enzymatic Study

Cipla made effervescent tablets of N-Acetyl-Cysteine (mucinac 600) were purchased from commercially available sources. Based on the quantity of NAC present in the tablet, $1\times10^{-1}$M tablet solution was prepared in 10 mM aq. HEPES buffer solution (pH7). Enzyme solution was prepared according to the requirement by dissolving 1 mg/ml in 10 mM aq. HEPES buffer solution (pH7). A fixed concentration of NAC (200 equiv.) was added to the 10 μM probe in HEPES: ACN (9:1). Since 1 mg of solid enzyme contains 3301 units of protein and 1 unit can hydrolyse 1 μM of substrate, accordingly enzyme concentration was varied with respect to the substrate concentration.

Example 6: General Procedure for Confocal Studies

Hct116 cells ($3\times10^5$) (ATCC® CCL247™) were seeded on cover slips placed in 6 well plates. After 24 hours, cells were treated with L (10 μM) for 30 minutes. Cells were then washed thrice with Phosphate Buffer Saline (1×PBS) and fixed with 4% PFA for 20 minutes and washed again with 1×PBS. Nail paint was used to seal the cover slips mounted on the glass slides. Images were acquired in Olympus Fluoview Microscope.

Example 7: In Vitro Cytotoxicity of L on Hct116 Cells

The in vitro cytotoxicity of L on Hct116 cells (Colon cancer cell) were determined by conventional MTT (3-(4, 5-Dimethylthiazol-2-yl)-2, 5-diphenyltetrazolium bromide, a yellow tetrazole) assay. Hct116 colon cancer cells ($7\times10^3$) were seeded in each well of a 96 well plate and cultured in a 37° C. incubator supplied with 5% $CO_2$. Cells were maintained in DMEM medium, supplemented with 10% Foetal Bovine Serum and 100 Units of Penicillin Streptomycin antibiotics. After 24 hours the cells were treated with different concentrations of the L in triplicates for 12 hours. After treatment cells were added with 0.5 μg/ml of MTT reagent. The plate was then incubated for 4 hours at 37° C. 100 μl of Isopropyl Alcohol was added to each well. Optical density was measured at 570 nm using Multiskan Go (Thermo Scientific) to find the concentration of the cell inhibition. $IC_{50}$ value has been calculated to be 100 μM.

The formula used for the calculation of the MTT assay for evaluation of the cell viability was as follows:

Cell viability (%)=(means of Absorbance value of treated group/means of Absorbance value of untreated control)×100.

ADVANTAGES OF INVENTION a) Simple process of detection b) Selective determination of free cysteine c) This method is of much practical significance in real time monitoring as it could be done without the aid of any instruments.

We claim:

1. A process for the preparation of compound of formula (L) comprising the steps of:
 (i) Refluxing boron-dipyrromethene (BODIPY) of formula R" with 4-hydroxybenzaldehyde, piperidine and glacial acetic acid in toluene to obtain compound of formula R';

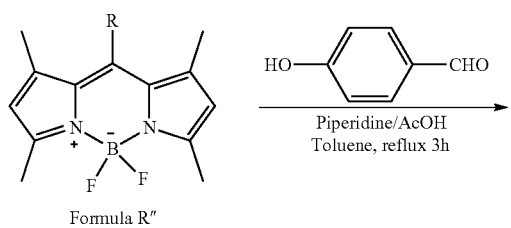
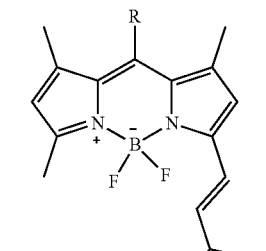
Formula R'
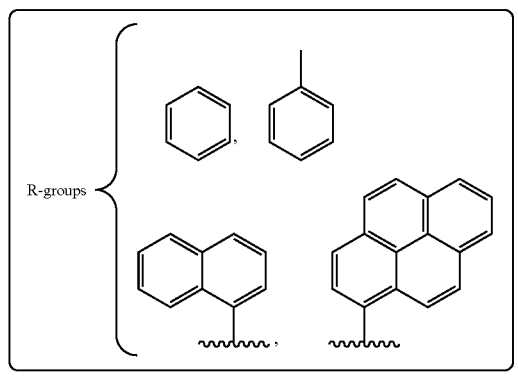
(ii) Reacting the compound of formula R' with acryloyl chloride in dichlotomethane (DCM) at room temperature to obtain ligand of formula (L)
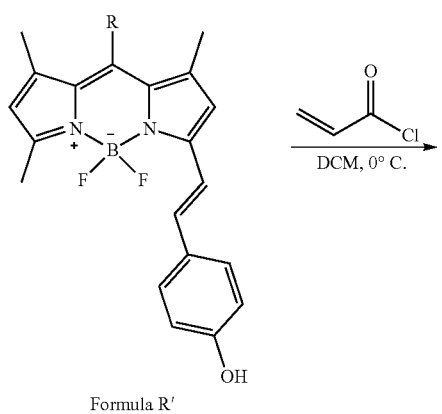
Formula R'
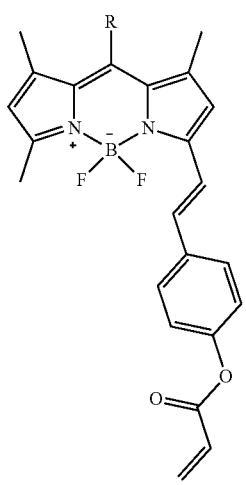
wherein R represent phenyl, toluene, naphthalene and pyrene.
2. A compound for selective determination of free cysteine having general formula (L) prepared by the process as claimed in claim 1
Formula L Wherein R is selected from
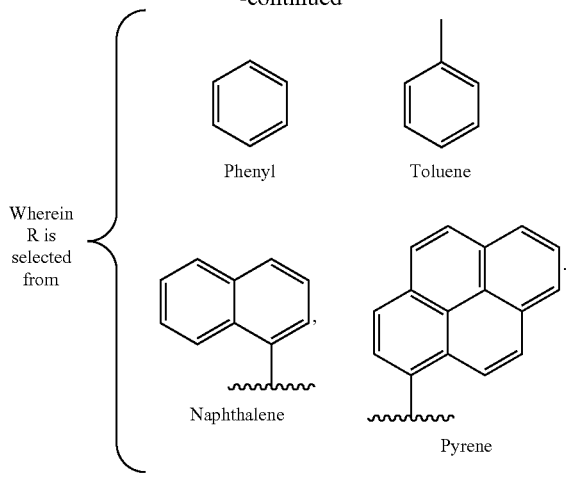
Phenyl, Toluene, Naphthalene, Pyrene.
3. The compound as claimed in claim 1 wherein the compounds of formula (L) comprises:
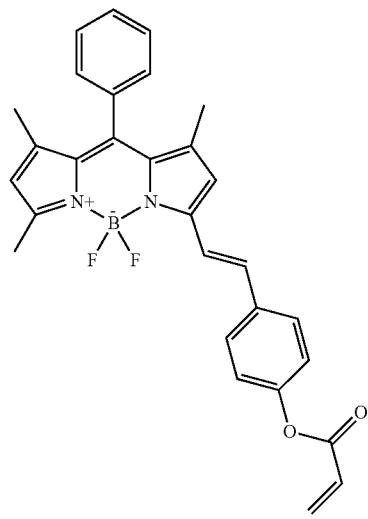
A
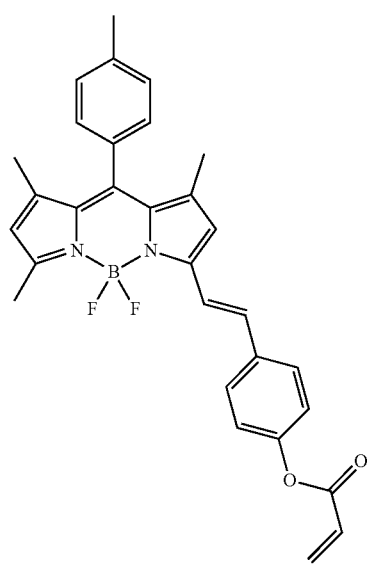
B
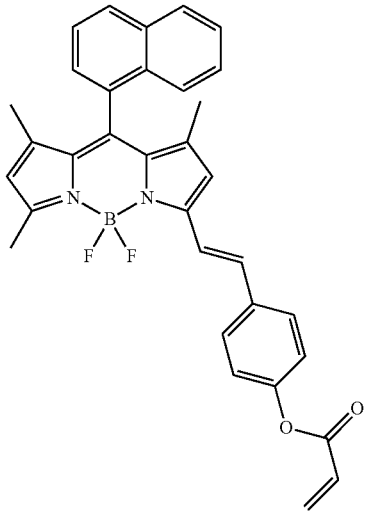
C
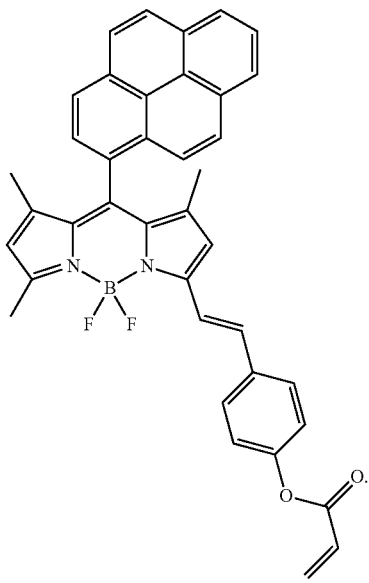
D
4. A method for selective detection of free cysteine, said method comprising;
   i. Dissolving 500 μl of $1 \times 10^{-4}$ M of ligand of formula (L)
Formula L
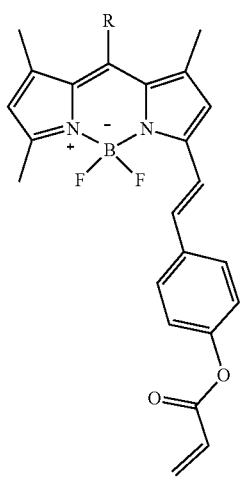

-continued

Wherein R is selected from

Phenyl

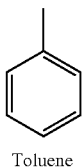
Toluene

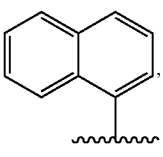
Naphthalene

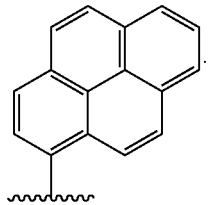
Pyrene in 4.5 ml of 10 mM HEPES aqueous buffer medium of pH 7.2 to obtain $1\times10^{-5}$ M ligand concentration;

ii. preparing the stock solution of $1\times10^{-2}$ M analytes in aqueous HEPES buffer medium at pH 7.2;

iii. thin layer chromatography (TLC) test strips; and iv. performing photo physical studies selected from fluorescence assay, MTT assay and Ultraviolet-visible spectroscopy for detection of free cysteine in HEPES: acetonitrile medium (9:1, v/v) at pH 7.2 as per instruction manual.

* * * * *